United States Patent [19]

Fecondini

[11] Patent Number: 4,994,026
[45] Date of Patent: Feb. 19, 1991

[54] GRAVITY FLOW FLUID BALANCE SYSTEM

[75] Inventor: Luciano Fecondini, Bologna, Italy

[73] Assignee: W. R. Grace & Co. - Conn., Lexington, Mass.

[21] Appl. No.: 238,903

[22] Filed: Aug. 31, 1988

[51] Int. Cl.$^5$ .............................................. A61M 1/03
[52] U.S. Cl. ........................................ 604/29; 604/6; 604/31
[58] Field of Search ....................... 604/4–6, 604/29–31, 65

[56] References Cited

U.S. PATENT DOCUMENTS

| | | |
|---|---|---|
| 2,718,982 | 9/1955 | Long . |
| 2,919,695 | 1/1960 | Kim . |
| 3,410,268 | 11/1968 | Leucci . |
| 3,552,393 | 1/1971 | Willgeredt . |
| 3,585,995 | 6/1971 | Perkins . |
| 3,655,123 | 4/1972 | Judson et al. .................... 604/6 |
| 3,730,183 | 5/1973 | Goldsmith et al. ............... 604/29 |
| 3,783,866 | 1/1974 | Tirkkonen ....................... 604/29 |
| 3,802,432 | 4/1974 | Djerassi ......................... 604/6 |
| 3,920,014 | 11/1975 | Banko . |
| 4,007,742 | 2/1977 | Banko . |
| 4,096,859 | 6/1978 | Agarwal et al. ................. 604/29 |
| 4,137,915 | 2/1979 | Kamen . |
| 4,190,047 | 2/1980 | Jacobsen et al. ................ 604/29 |
| 4,204,957 | 5/1980 | Weickhardt ..................... 604/5 |
| 4,240,408 | 12/1980 | Schael .......................... 604/29 |
| 4,261,360 | 4/1981 | Perez . |
| 4,275,726 | 6/1981 | Schael . |
| 4,291,692 | 9/1981 | Bowman et al. . |
| 4,411,649 | 10/1983 | Kamen . |
| 4,412,917 | 11/1983 | Ahjopalo ........................ 604/29 |
| 4,449,538 | 5/1984 | Corbitt et al. . |
| 4,457,750 | 7/1984 | Hill . |
| 4,466,804 | 8/1984 | Hino . |
| 4,529,397 | 7/1985 | Hennemuth et al. . |
| 4,600,401 | 7/1986 | Kamen . |
| 4,650,457 | 3/1987 | Morioka et al. . |
| 4,650,458 | 3/1987 | Dahlberg et al. . |
| 4,650,464 | 3/1987 | Ruiz et al. . |
| 4,657,529 | 4/1987 | Prince et al. . |
| 4,728,433 | 3/1988 | Buck et al. . |
| 4,747,822 | 5/1988 | Peabody ......................... 604/31 |
| 4,767,399 | 8/1988 | Bollish .......................... 604/6 |

FOREIGN PATENT DOCUMENTS 3213390 10/1983 Fed. Rep. of Germany .......... 604/4

OTHER PUBLICATIONS

Amicon Equaline Fluid Control System, Publication No. 261, W. R. Grace & Co., 1988.

Primary Examiner—Stephen C. Pellegrino
Assistant Examiner—Ralph A. Lewis
Attorney, Agent, or Firm—Hale and Dorr

[57] ABSTRACT

Disclosed is a gravity flow fluid balancing system that includes an infusion line to transport an infusate from an infusate supply to a patient's body and an ultrafiltrate line for transporting ultrafiltrate from the body to an ultrafiltrate reservoir. The infusate and ultrafiltrate reservoirs are each connected to a load cell. The load cells are, in turn, connected to a control unit which compares the readings received from the load cells. A clamp, which is controlled by the control unit, controls the flow out of the infusate reservoir into the patient's body. Control of the clamp and fluid flow through the system can be regulated on a weight change basis (infusate - ultrafiltrate) or on an infusion basis.

12 Claims, 10 Drawing Sheets

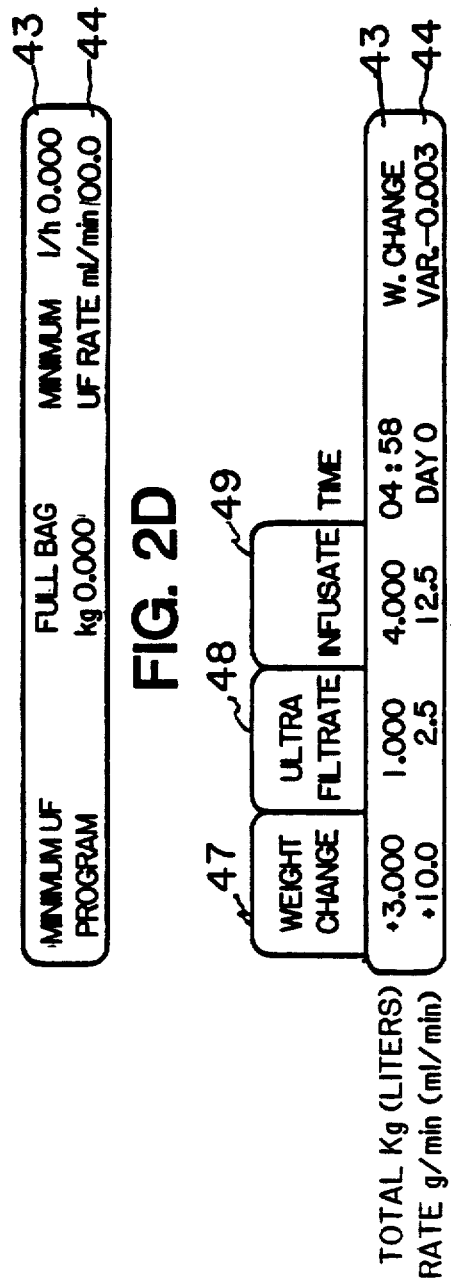
FIG. 2D
FIG. 2E
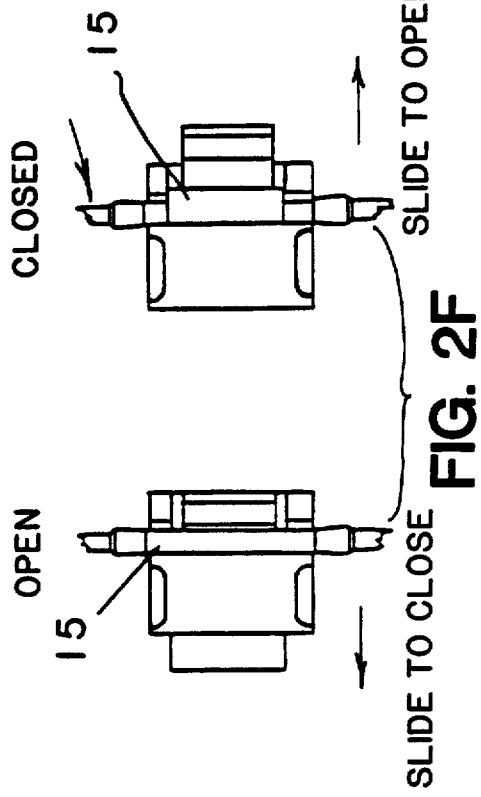
FIG. 2F

GRAVITY FLOW FLUID BALANCE SYSTEM

BACKGROUND OF THE INVENTION

The present invention relates to a system for balancing fluids in a human body and more particularly to a gravity flow system for monitoring and controlling fluid removal and fluid infusion to a patient.

Most known systems for monitoring and controlling fluid removal and infusion into a patient's body control only the infusion of fluids at a controlled rate and cannot control a patient's fluid dynamic state in total. Known fluid removal and infusion systems also do not control the flow of fluids to and from the body in a very accurate manner. One common technique used by most of these known monitoring systems involves counting drops, but such systems are sensitive to variations in drop size caused by temperature and viscosity, drop rate and manufacturing accuracy of the drop platform.

Other generally more accurate commercially available systems depend on use of a pump to control either the infusion of fluid or the balancing of fluids in the patient's body. The accuracy required of the pumps, however, greatly increases the cost of such systems.

It is therefore a principal object of the present invention to provide a gravity flow system for balancing body fluids in a very accurate manner.

Another object of the present invention is to provide a gravity flow system for balancing body fluids that is substantially cheaper to manufacture than systems utilizing pumps.

It is another object of the present invention to provide a gravity flow system for balancing body fluids which allows an operator to select one of several modes of operation.

SUMMARY OF THE INVENTION

Accordingly, the gravity flow fluid balancing system of the present invention includes an infusion line to transport an infusate from an infusate supply to a patient's body and an ultrafiltrate line for transporting ultrafiltrate from the body to an ultrafiltrate reservoir. The infusate and ultrafiltrate reservoirs are each connected to a load cell. The load cells are, in turn, connected to a control unit which compares the readings received from the load cells. A clamp, which is controlled by the control unit, controls the flow out of the infusate reservoir into the patient's body. Control of the clamp and fluid flow through the system can be regulated on a weight change basis (infusate-ultrafiltrate) or on an infusion basis.

These and other objects and features of the present invention will be more fully understood from the following detailed description which should be read in light of the accompanying drawings and which corresponding reference numerals refer to corresponding parts throughout the several views.

BRIEF DESCRIPTION OF THE DRAWINGS

FIGS. 2b-2e are top views of the display shown in FIG. 2a in the various modes of system operation.

FIG. 2f is a plan view of the clamp mounted on the display shown in FIG. 2a;

DETAILED DESCRIPTION OF THE PREFERRED EMBODIMENTS

Figure 1:
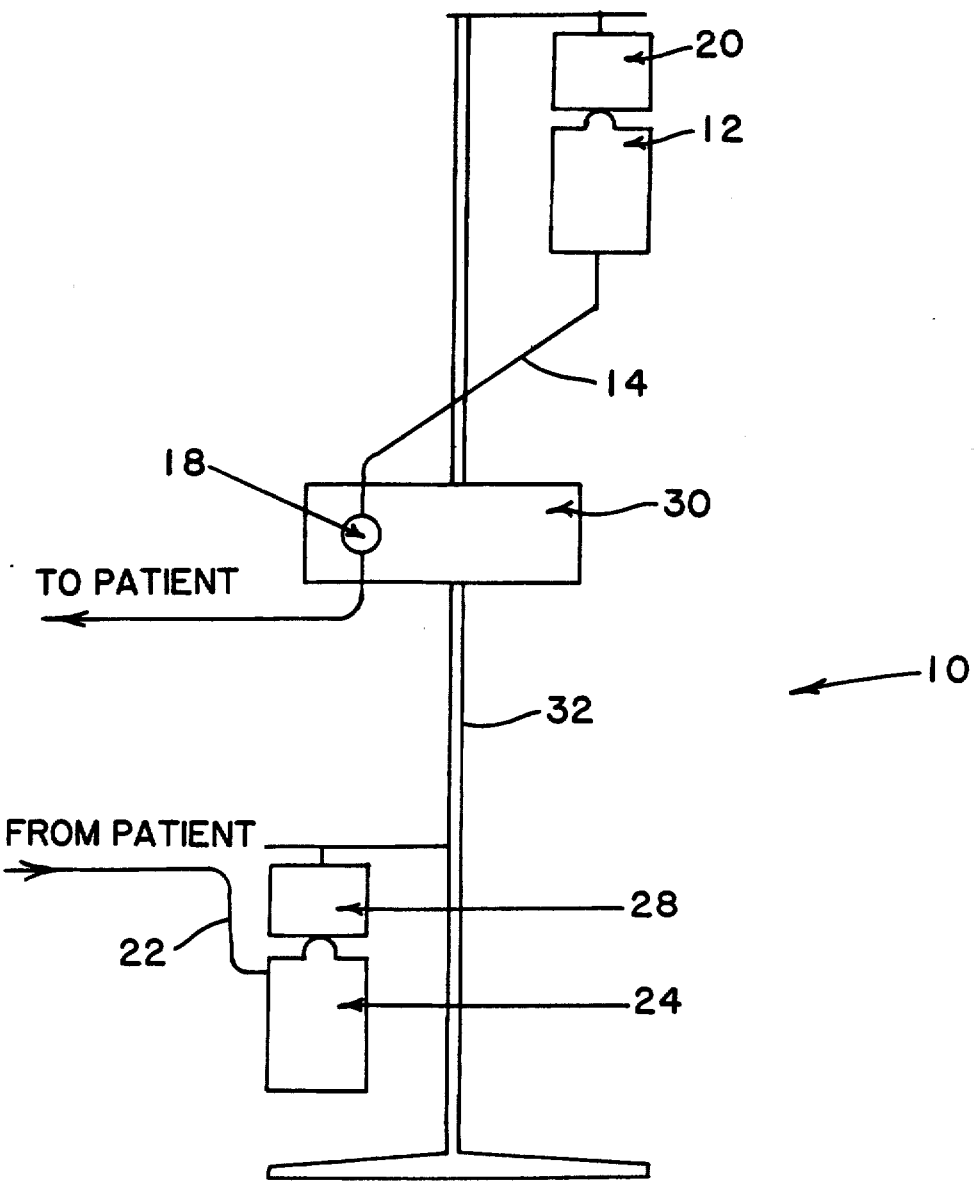
FIG. 1 is a schematic view of the components of the system of the present invention.

Referring to FIG. 1, the fluid balancing system 10 of the present invention includes an infusate reservoir 12 which is connected to a first fluid conduit or line 14 which in turn is connected to the body of patient 16 in a manner that will enable fluid travelling through line 14 to enter the patient's body. As this system is a gravity flow system the infusate reservoir is mounted at a location above the patient. A clamp 18 surrounds the line 14 in order to control the quantity of infusate flowing from the reservoir 12 to the body 16 by expanding or contracting around the line 14 to increase or decrease the effective diameter of the passage through the line 14. The infusate reservoir 12 is connected to a load cell 20 which continually measures the weight of the infusate reservoir.

The fluid balancing system also includes an ultrafiltrate conduit or line 22 which carries fluid being removed from the body 16 to an ultrafiltrate reservoir 24. An ultrafilter 26 is provided within the ultrafiltrate conduit 22 in order to filter fluid passing through this conduit. The ultrafilter 26 is connected to line 22 at a height below the height at which line 22 is connected to the patient's body and at a height above the ultrafiltrate reservoir 24. Load cell 28 supports and determines the weight of the ultrafiltrate reservoir 24. Control unit 30 on which clamp 18 is preferably mounted also includes a display 31 and a microprocessor for processing the weight signals received from load cells 20, 28. The load cells 20, 28 and the control unit are mounted on stand 32.

The system described above monitors and precisely controls fluid balance in a patient undergoing continuous fluid removal (e.g. continuous arteriovenous hemofiltration (CAVH)) and/or continuous fluid replacement (infusion). The system can also monitor ultrafiltration without infusion or can monitor and control infusion without simultaneous fluid removal.

Figure 2A:
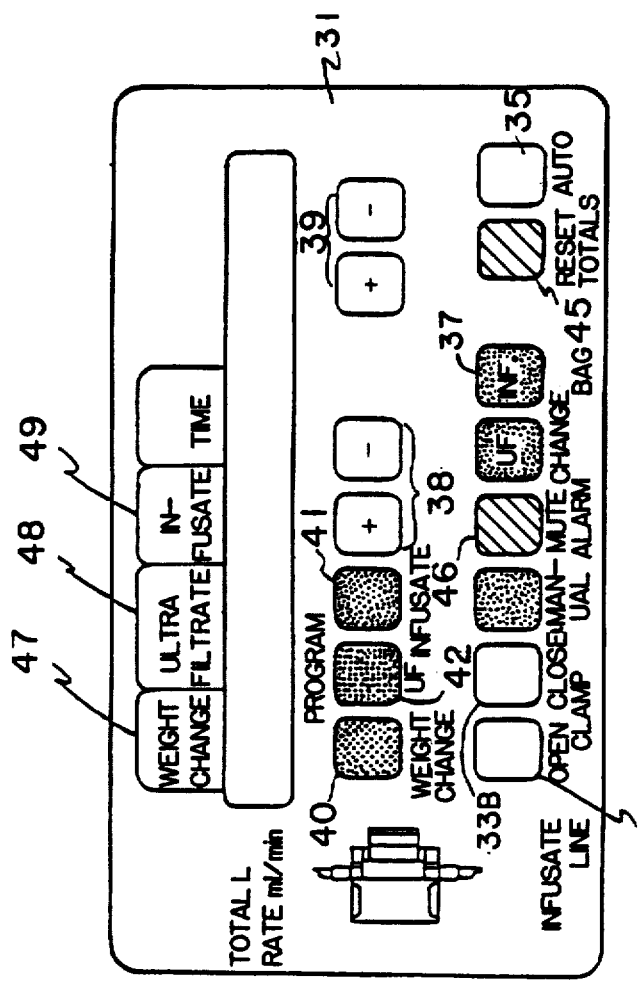
FIG. 2a is a top plan view of a display and keyboard utilized by the system shown in FIG. 1.

Once the system is powered up, the microprocessor runs through preliminary tests to initially determine that the system (in particular, the load cell and battery) is operating properly. An operator pushes the RESET TOTALS key twice and then connects reservoirs 12, 24 to load cells 20, 28 respectively. In the embodiment shown, the reservoirs 12, 24 are plastic bags, and they are mounted to hooks connected to the load cells in a manner which allows the bags to hang down freely without touching the stand 32 or any other part of the equipment so as to avoid any influences on the weight readings. With a twisting motion, the operator inserts a pin into the infusate reservoir 12 without venting reservoir 12. The infusate line 14 is then closed using manual roller 34 in the line. The operator then opens clamp 18 using OPEN CLAMP key 33a, and before closing places the conduit tubing 14 inside the clamp housing (See FIG. 2f). The tubing 14 includes a silicone segment 15 which fits within the clamp housing. In a preferred embodiment, the tubing has a 3 mm internal diameter and a 4.1 mm external diameter. Before placing the silicone segment 15 into the slot, the silicone section is stretched. The sliding piece 18a of the clamp 18 is then moved to the closed position, and the CLOSE CLAMP key 33b is pushed. The manual roller on the line is then once again opened.

An AUTO key 35 on a control panel 31 is pressed to initiate automatic control of the system. During operation, if a fluid bag needs to be changed the UF or INF CHANGE BAG key is pushed and while keeping the pole stable a new bag is mounted. Once oscillation of the bags stops, the appropriate CHANGE BAG key is once again pushed.

Once under automatic control, the system automatically controls the infusing line according to the selected program. In WEIGHT CHANGE mode, the system drives clamp 18 so as to obtain the programmed weight change. Under this mode the actual infusion rate depends on the ultrafiltration rate. In the INFUSION mode, the system drives clamp 18 so as to obtain the programmed infusion regardless of the ultrafiltration rate. When operating in either mode, the system controls operation according to a set point target. This target is automatically calculated by multiplying the programmed rate by the elapsed time. The difference between the set point and the actual value of the controlled variable is displayed as a variance. If the variance exceeds ±0.100 kg or liters, an audible alarm is triggered, but the machine continues operation while trying to reduce the variance.

The system of the present invention also includes several alarms which will alert the system operator to system malfunctioning. A load alarm can be activated if any one of several conditions is met. For example, if a load cell is disconnected, an alarm will be triggered. If a negative load change occurs (i.e. the infusate load increases or the ultrafiltrate load decreases with respect to their initial tare by more than 25 grams), then the load alarm will also be triggered. This negative load change occurs when the ultrafiltrate or infusate bag is incorrectly installed, or when the UF or INF CHANGE BAG function was terminated and tare was ascertained. Thirdly, the load alarm is triggered when load cell connections are inverted, i.e. the infusate load cell cable and the ultrafiltrate load cell cable are connected to the wrong connections.

The system of the present invention may be programmed to determine fluid balance during treatment by presetting an infusion or weight change operating mode. Setting one of the modes excludes the other. If infusion rate is programmed, weight change rate is automatically deleted and vice versa. When deleted, the display under that value is blank. The relationship between the values is:

weight change = infusate − ultrafiltrate.

Figure 2B:

To program the system so that the fluid balance is determined by weight change, the operator initially pushes the program key 40 labeled WEIGHT CHANGE and then inputs the desired weight change and its rate in milliliters per minute or liters per hour. To adjust the total weight change on the display (FIG. 2b) the left set of ± keys 38 are used. The right set of ± sign keys 39 are used to enter the desired weight change rate. Positive total and rate values on the display mean weight gain and negative values mean weight loss. The totals entered during these programming steps do not drive the treatment. They are required by the processor for comparison with data obtained from load cells 20, 28 during treatment. When the pre-set total weight change is reached, the machine gives an audible alarm and shifts treatment to rate=0. In case no weight change is desired (ultrafiltrate=infusate), it is necessary to program a weight change rate of 0.

Figure 2C:

To determine the fluid balance using the infusion mode, the operator inputs the desired infusion rate in milliliters per minute or liters per hour and the display (FIG. 2c) will indicate both the total and rate automatically. The INFUSATE key 41 is then pressed to obtain a desired empty bag value on the display by using the left set of ± keys 38, and the right set of ± keys 39 is used to enter the desired infusion rate.

If a minimum ultrafiltration rate is required, the ULTRAFILTRATE key 42 is pressed to enter this value in milliliters per minute using the right set of ± keys 39. A full bag value can be programmed with the left set of keys 38 (see FIG. 2d). Total ultrafiltrate rate is not programmable as it is not under the machine control. When a minimum rate is programmed, the unit will give an audible alarm if the average rate over a ten minute period drops below that rate.

When one of the keys WEIGHT CHANGE, ULTRAFILTRATE or INFUSATE 40, 42, 41 are pushed, the unit displays the last programmed values.

During operation, the display shows a lapse of time on two lines: hours and minutes on the top line 43 and days on the second line 44. The right side of the display indicates whether the system is in automatic (AUTO) or manual (MANUAL) operation.

In operation, the upper line on the right end of the display (see FIG. 2e) indicates whether the unit is in the weight change (W.C.) or infusate (INF) control mode. Below that indication there is a continuing display of the variance (VAR) between programmed and actual total weight change or infusion values.

A RESET TOTAL key 45 clears the display for the start of treatment. This deletes all previously accumulated data except the program. To avoid accidental loss of data, the controller asks for reconfirmation on the display, and reconfirmation requires a second push of the RESET key before clearance.

The system also includes several safety precautions. In case of power interruption or connection failure, the unit shifts to battery operation which is indicated on the display. The battery is recharged during normal functioning and will last for about one hour without external power. Before stopping the machine will give an audible alarm.

In the case of any significant variance from the programmed values (100 g above or below programmed values) which might be due to obstruction in the infusion line, a sudden shift of the load cell weight, etc., the system gives an audible alarm and displays the word LIMIT under the position of the parameter which caused the alarm. This promptly indicates to the operator where to take action. During the alarm situation, the control system continues to manage the treatment by compensating to recover the program equilibrium. To turn off the alarm, the MUTE ALARM key 46 is pushed. If the cause has not been removed within one minute, the audible alarm will start again.

Figure 3A:
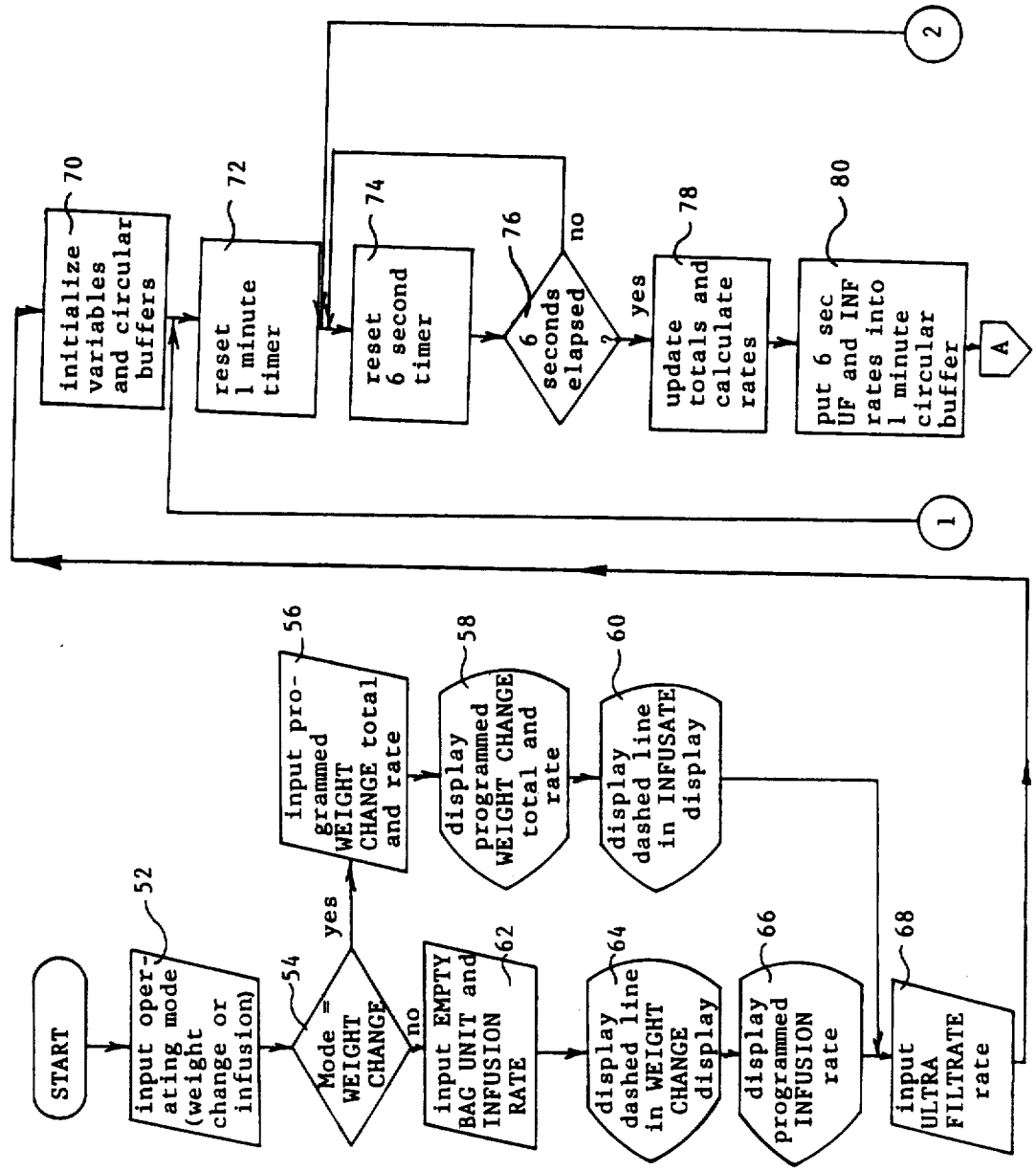
FIGS. 3a-3b are flow charts of the operation of the system shown in FIG. 1.
Figure 3B:
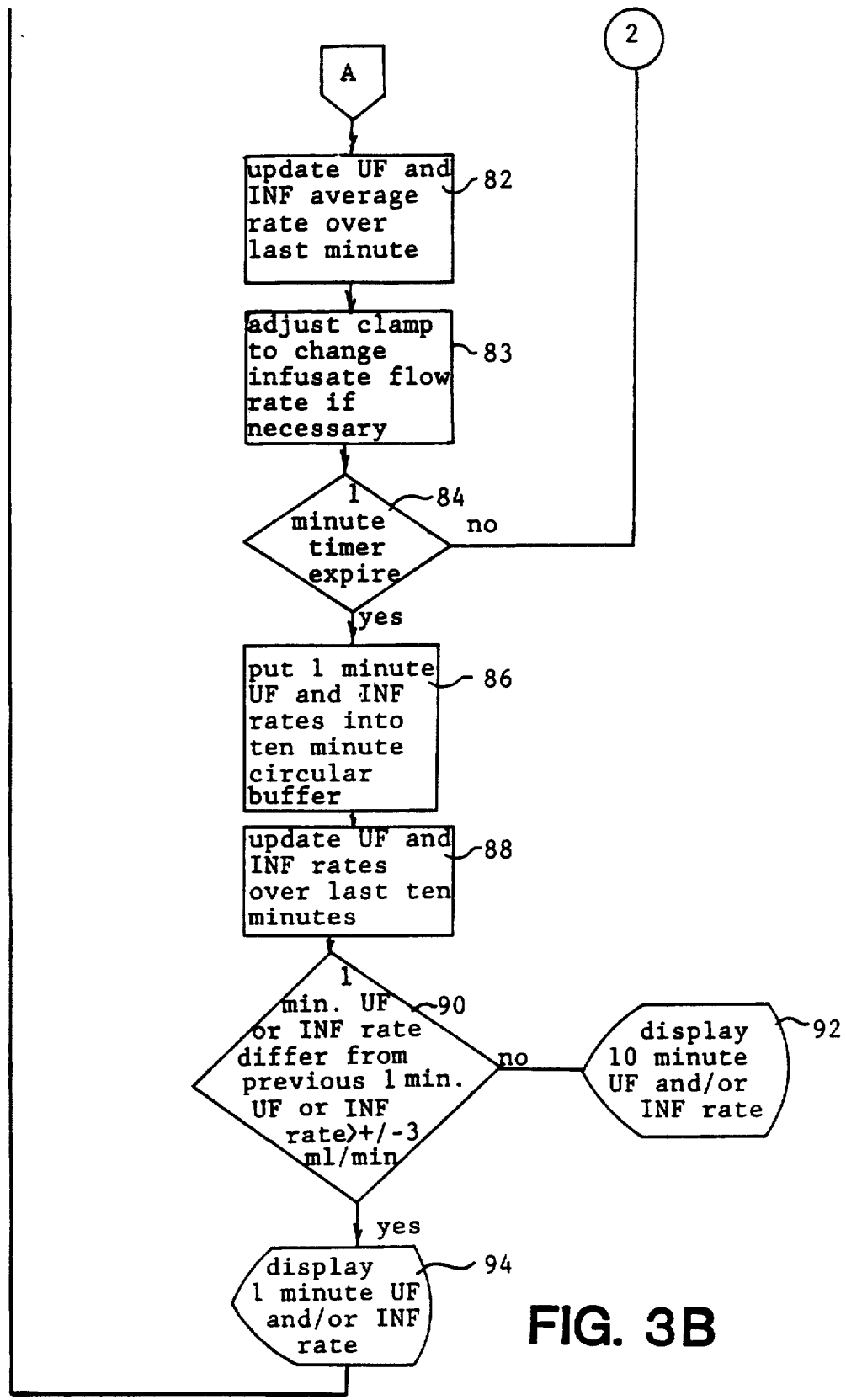

Referring to FIGS. 3a–3b the system operation will now be described. Initially, the system in step 52 requests the operator to indicate whether the system will be operating in the WEIGHT CHANGE or INFUSION mode. In the WEIGHT CHANGE mode, the fluid balance will be maintained by using the relationship:

$$\text{weight change} = \text{infusate} - \text{ultrafiltrate}.$$

After selecting the operating mode, the operator programs the desired total weight change as well as the desired rate of weight change. The weight change values calculated by the system are constantly compared to these preset weight change values, and if any of the values are exceeded, an alarm will be triggered. To operate under the INFUSION mode, the operator also sets the empty bag value and the infusate rate.

After determining the mode, in step 54 the system shifts operation according to whether the WEIGHT CHANGE or INFUSION mode is selected. If WEIGHT CHANGE is selected, in step 56, the programmed weight change total and rate are input to the system. In step 58, the system then displays the weight change total and rate in the weight change section 47 of the display 40. In order to make it clear that the system is operating in the WEIGHT CHANGE mode, the system displays a set of dashed (--) lines in the INFUSATE section 49 of the display 31 in step 60.

If the system is operating in the INFUSION mode, the operator provides the empty bag limit and an infusion rate in step 62. In step 64 to make it clear that the system is operating in the infusion mode, the system displays a set of dashed (--) lines in the weight change portion 47 of the display 31, and the infusion rate is displayed in the lower row 44 of the infusate section 49 of the display 31. Whether the system is operating in the weight change or infusion mode, the operator enters the minimum ultrafiltrate rate desired in step 68.

Once the system has been programmed, the system in step 70 initializes all variables and clears the several circular buffers that are used for storing ten measurements from ten previous time periods. In the preferred embodiment, the system includes one circular buffer for values that it calculates every six seconds and a second circular buffer for values it calculates every minute. This enables the system to easily calculate average values over a one minute length of time and average values over a ten minute time period.

In steps 72 and 74 a one minute timer and a six second timer are reset. In step 76, the system tests whether the six second timer has elapsed so that a new reading of the selected variables can be taken every six seconds. If the six seconds have elapsed, the system in step 78 will update the totals and calculate rates as will be described below with reference to FIG. 4. In step 80 the system places the calculated ultrafiltrate and infusate rates into the respective one minute circular buffers and in step 82 the ten (10) six-second values in the ultrafiltrate and in the infusate one minute circular buffers are averaged to provide one minute averages of the ultrafiltrate rate and of the infusate rate. If the calculated rates differ from the programmed rates, the system adjusts the flow of infusate by adjusting the clamp to increase or decrease the opening through the silicone segment 15 of tubing 14 in step 83. In step 84 the system checks to see if the one minute timer has expired and if it has not, control returns to step 74 and a new set of six second readings is taken. If the one minute timer has expired, the one minute ultrafiltrate and infusate averaged rates are placed into the respective ultrafiltrate and infusate ten minute circular buffers in step 86 and the ten values in each of the two buffers are averaged to provide averaged ultrafiltrate and infusate rates over the last ten minutes of the system operation in step 88. The system then displays the ultrafiltrate and infusate rate. Prior to displaying a rate the system, in step 90, determines whether or not the current one minute ultrafiltrate and infusate rates differ from the immediately preceeding one minute ultrafiltrate and infusate rates by more than + or − three milliliters per minute. If it does not, the system in step 92 displays the ten minute average ultrafiltrate and/or infusate rates. If either rate does differ by more than + or − three milliliters per minute, the system displays the one minute ultrafiltrate and/or infusate rate in step 94. After displaying the ultrafiltrate and infusate rates, system operation returns to step 72.

Figure 4:
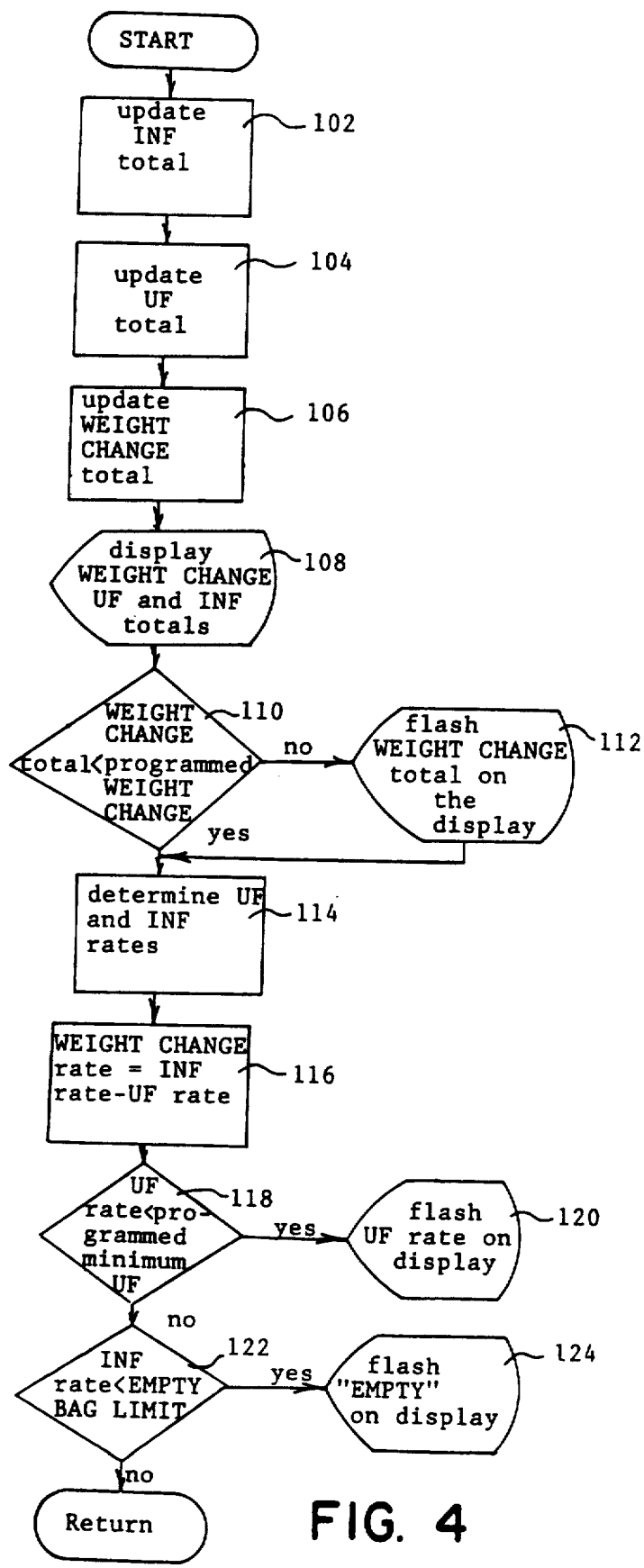
FIG. 4 is a more detailed flow chart of the updating and calculating functions performed by the system of FIG. 1.

Referring now to FIG. 4, the updating of the totals and the calculation of the rates will now be described. In steps 102 and 104 the system updates the infusate total and ultrafiltrate total by obtaining new readings from the load cells. In step 106, the weight change total is updated by subtracting the ultrafiltrate total obtained in step 104 from the infusate total obtained in step 102. In step 108 the system then displays the weight change, ultrafiltrate and infusate totals on the first line of the display. In step 110, the weight change total is compared to the programmed weight changes, and if the actual weight change is greater than the programmed limit, the display flashes the weight change total on the display to indicate to the operator that the limit has been exceeded. If the weight change is less than the programmed weight change, the system calculates the ultrafiltrate and infusate rates in milliliters per minute in step 114. The weight change rate is then calculated in step 116 as being equal:

$$\text{infusate rate} - \text{ultrafiltrate rate}.$$

In step 118 the system compares the ultrafiltrate rate with the programmed minimum ultrafiltrate rate. If the actual ultrafiltrate rate is less than the programmed minimum ultrafiltrate rate, the system flashes the ultrafiltrate rate on the display in step 120. In step 122, the system compares the infusate rate with the empty bag limit, and if the infusate rate is less than the empty bag limit, the system flashes the word EMPTY in the rate row of the INFUSATE section 49 of the display 40. After the totals have been updated and the rates have been calculated, control returns to the main program which has been described above with reference to FIGS. 3a–3b.

Figure 5:
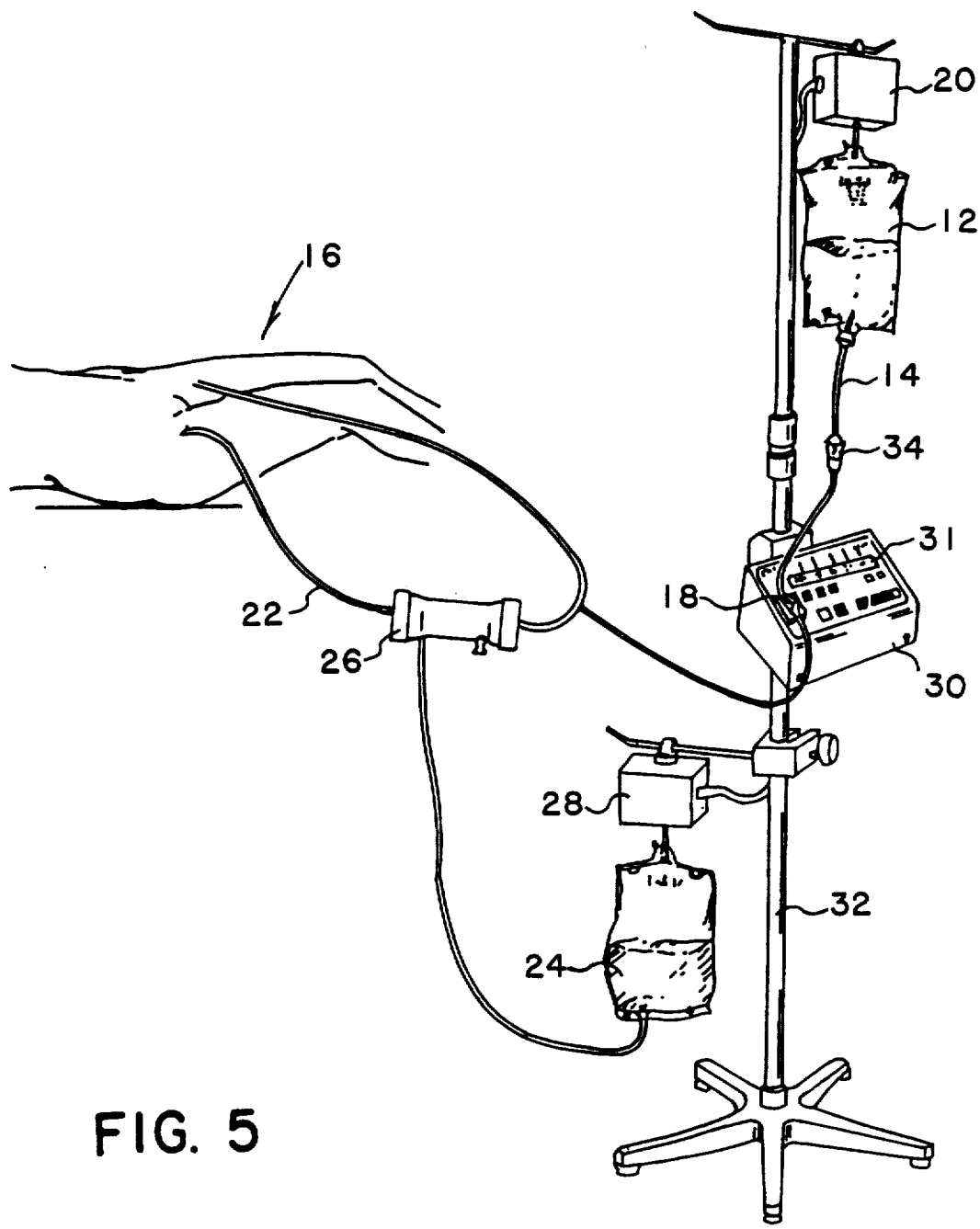
FIGS. 5-8 are perspective views of the system of FIG. 1 as used in practical applications.
Figure 6:
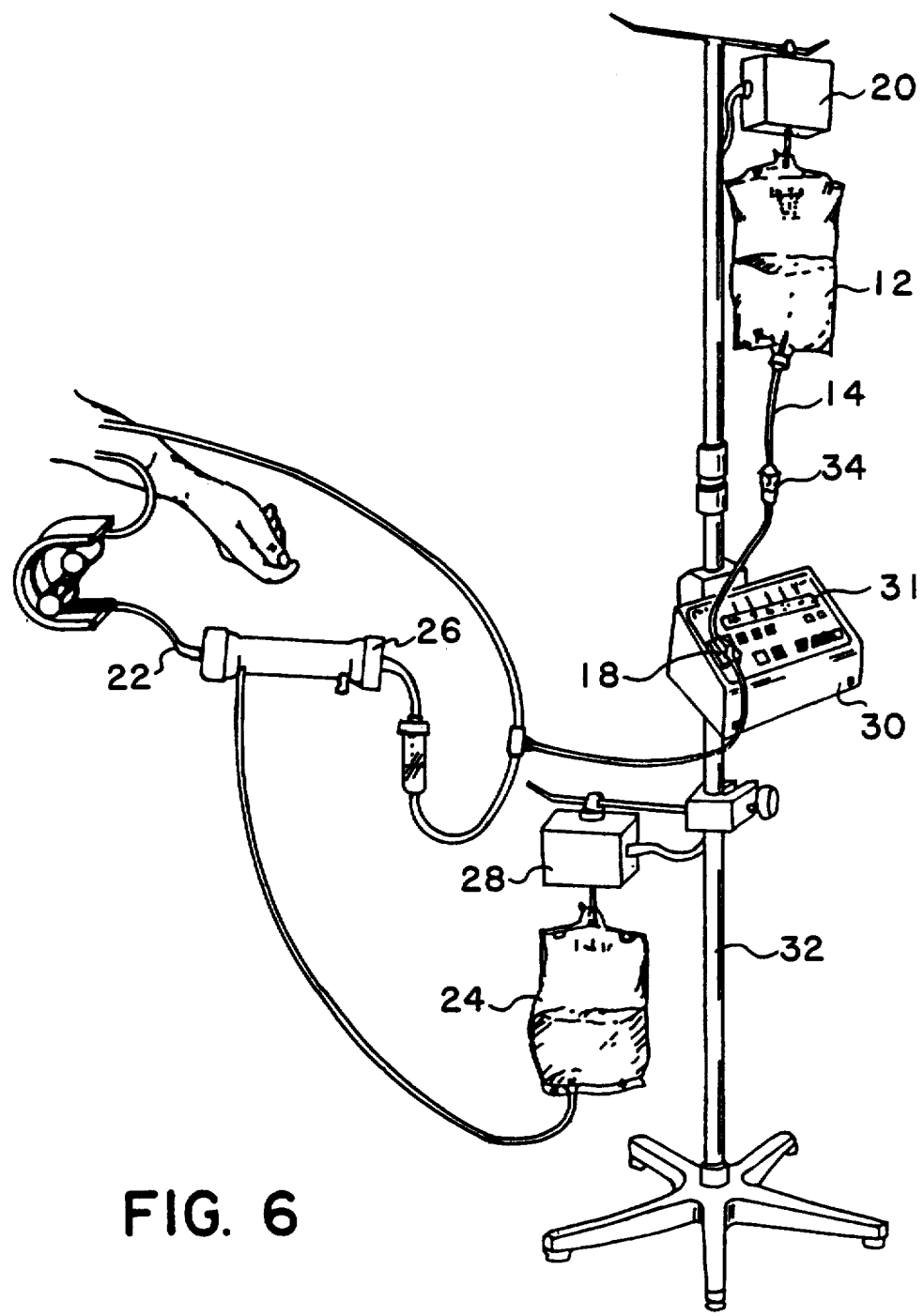
Figure 7:
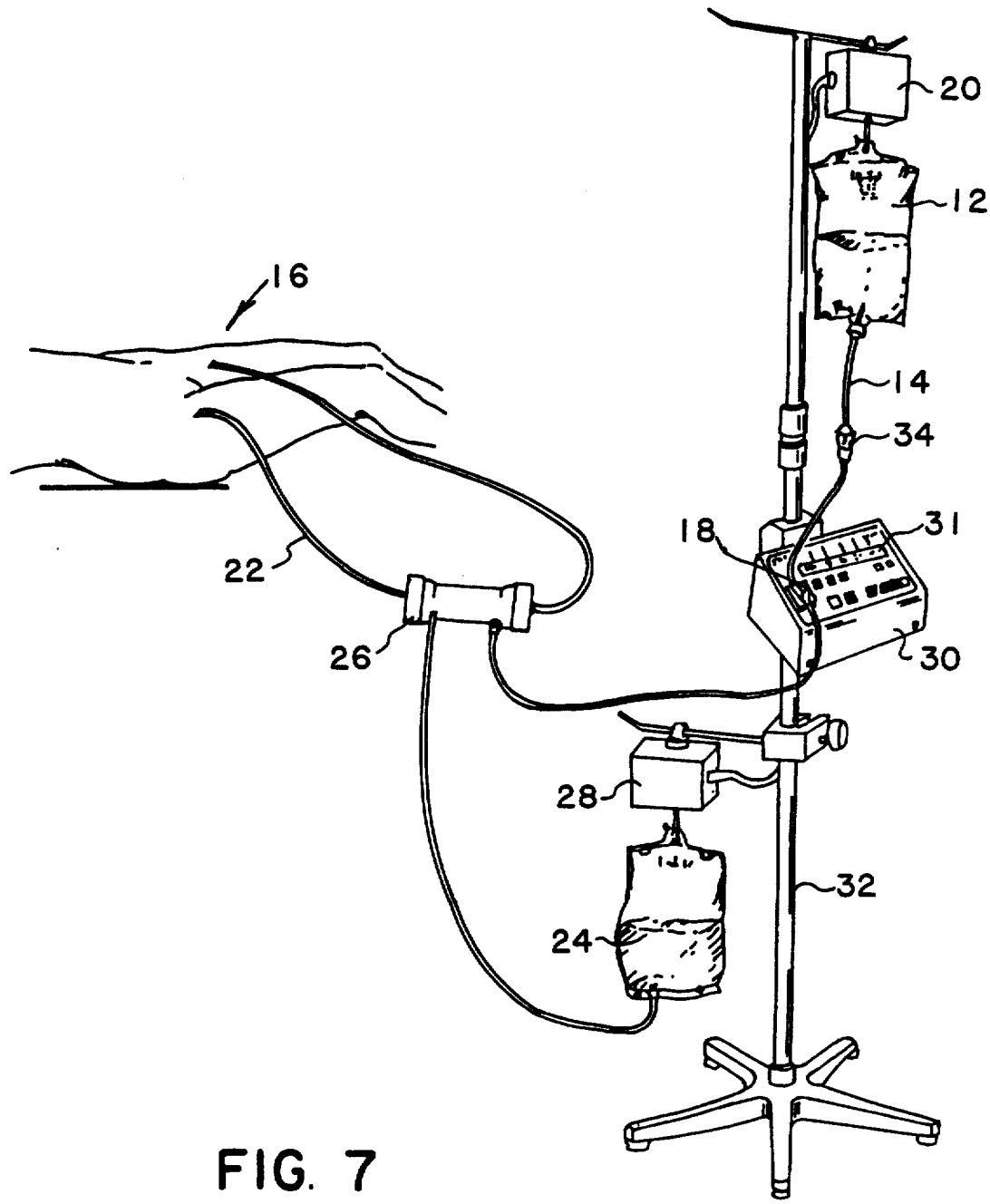
Figure 8:
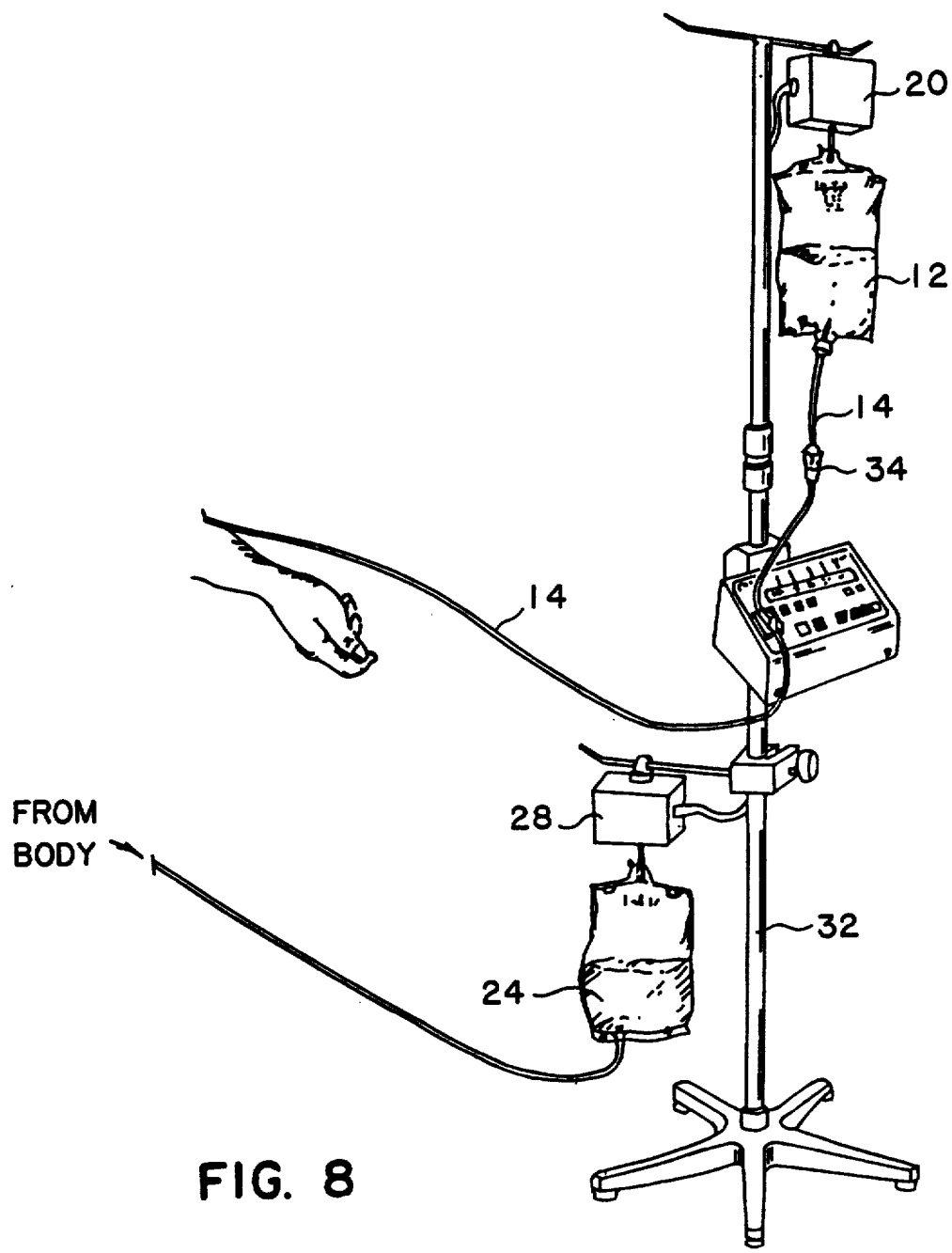

Referring to FIGS. 5–8, several uses of the system described above are illustrated. In FIG. 5 the system is shown as being used in a continuous arterial venous hemofiltration (CAVH) application in which the system (operating in the WEIGHT CHANGE mode) monitors the ultrafiltrate removed from the patient and controls the amount of infusate in order to maintain the weight change that has been programmed for the patient. In FIG. 6, a continuous venous hemofiltration application is shown in which when pumped hemofiltration is performed, the system (operating in the WEIGHT CHANGE mode) manages a treatment exactly in the same way as with the application shown in FIG. 5. In a continuous arterial venous hemofiltration dialysis application as shown in FIG. 7, when a sterile dialysate is used to increase clearances in a CAVH, the system (operating in the INFUSION mode) has to be programmed in order to give the required dialysate flow. Dialysate out is monitored, and the display 40 continuously shows the total patient weight change and the rate of the last minute. In FIG. 8, the system is shown in use for infusion or nutrition. The operation ranges from one ml/min to more than 100 ml/min. Often physicians will want to infuse exactly what the patient loses so that if the patient has a diuresis, this can be measured by the ultrafiltrate load cell and the system (operating in the WEIGHT CHANGE mode) will infuse the required quantity.

While the foregoing invention has been described with reference to its preferred embodiments, various alterations and modifications will occur to those skilled in the art. All such alterations and modifications are intended to fall within the scope of the appended claims.

What is claimed is:

1. A system for monitoring and controlling the infusion and removal of fluids travelling by gravity to a human body comprising:
    an infusate reservoir for storing a supply of infusate;
    means for transporting infusate from said infusate reservoir to the human body;
    an ultrafiltrate reservoir for storing a supply of ultrafiltrate;
    means for transporting a fluid from the human body to said ultrafiltrate reservoir, said means for transporting fluid including a means for filtering said fluid to obtain an ultrafiltrate;
    means for monitoring said infusate transported out of said infusate reservoir and the fluid transported to said ultrafiltrate reservoir by determining weight changes of said infusate reservoir and said ultrafiltrate reservoir;
    means for controlling the infusate transported out of said infusate reservoir based on a rate of weight change over time, said rate of weight change being equal to a rate of change over time in the weight of said infusate reservoir minus a rate of change over time in the weight of said ultrafiltrate reservoir.

2. The system for monitoring and controlling the infusion and removal of fluids travelling by gravity to a human body of claim 1 wherein said infusate reservoir is a bag supported at a height above the human body.

3. The system for monitoring and controlling the infusion and removal of fluids travelling by gravity to a human body of claim 1 wherein said means for transporting infusate comprises tubing of a length at least equal to the distance from said infusate supply to the human body and wherein said means for controlling the transported infusate or fluid comprises a closeable clamp mounted around said tubing.

4. The system for monitoring and controlling the infusion and removal of fluids travelling by gravity to a human body of claim 3 further comprising a processor for generating signals to control operation of said clamp in order to control the quantity of infusate transported from said infusate reservoir to the human body.

5. The system for monitoring and controlling the infusion and removal of fluids travelling by gravity to a human body of claim 4 wherein said means for monitoring the transported infusate and fluid comprises two load cells, one of said load cells being connected to said infusate reservoir to determine the weight of said infusate reservoir and the other of said load cells being connected to said ultrafiltrate reservoir to determine the weight of said ultrafiltrate reservoir, said load cells providing signals indicating the weight of said reservoirs to said processor.

6. The system for monitoring and controlling the infusion and removal of fluids travelling by gravity to a human body of claim 1 wherein said means for monitoring the transported infusate and fluid comprises two load cells, one of said load cells being connected to said infusate reservoir to determine the weight of said infusate reservoir and the other of said load cells being connected to said ultrafiltrate reservoir to determine the weight of said ultrafiltrate reservoir.

7. The system for monitoring and controlling the infusion and removal of fluids travelling by gravity to a human body of claim 4 wherein said means for monitoring the transported fluid further comprises a processor and means for providing weight-indicating signals to said processor from said load cells, said processor including means for calculating said rate of change in the weight of said infusate reservoir using a weight-indicating signal from said load cell connected to said infusate reservoir and means for calculating said rate of change in the weight of said ultrafiltrate reservoir using a weight-indicating signal from said load cell connected to said ultrafiltrate reservoir.

8. The system for monitoring and controlling the infusion and removal of fluids travelling by gravity to a human body of claim 1 further comprising means for setting a limit on a total weight change between said infusate reservoir and said ultrafiltrate reservoir.

9. The system for monitoring and controlling the infusion and removal of fluids travelling by gravity to a human body of claim 1 further comprising means for setting a minimum rate of flow of ultrafiltrate into said ultrafiltrate reservoir to be achieved by the system.

10. The system for monitoring and controlling the infusion and removal of fluids travelling by gravity to a human body of claim 1 wherein said ultrafiltrate reservoir is a bag supported at a height below the human body.

11. The system for monitoring and controlling the infusion and removal of fluids travelling by gravity to a human body of claim 1 further comprising means for displaying rates at which the weight of said infusate reservoir and of said ultrafiltrate reservoir change over time, said means for displaying including means for periodically changing the displayed rate with the changed rate being the average rate during a pre-set time interval if the changed rate is within a pre-selected range, and if the changed rate is outside said pre-selected range, the changed rate being the average rate during a shorter pre-set time interval.

12. A system for monitoring and controlling the infusion and removal of fluids travelling by gravity to a human body comprising:
    an infusate reservoir for storing a supply of infusate;
    means for transporting infusate from said infusate reservoir to the human body;
    an ultrafiltrate reservoir for storing a supply of ultrafiltrate;
    means for transporting a fluid from the human body to said ultrafiltrate reservoir, and means for transporting fluid including a means for filtering said fluid to obtain an ultrafiltrate;
    means for monitoring said infusate transported out of said infusate reservoir and the fluid transported to said ultrafiltrate reservoir by determining weight changes of said infusate reservoir and said ultrafiltrate reservoir;
    means for controlling the infusate transported out of said infusate reservoir based on a rate of weight change over time, said rate of weight change being equal to a rate of change over time in the weight of said infusate reservoir minus a rate of change over time in the weight of said ultrafiltrate reservoir;

means for controlling infusate transported out of said infusate reservoir based on a rate of flow of infusate over time from said infusate reservoir;

means for enabling either said means for controlling transported infusate based on said rate of weight change or said means for controlling transported infusate based on said rate of flow of infusate.

* * * * *